US00PP36474P2

(12) United States Plant Patent
Jachertz

(10) Patent No.: US PP36,474 P2
(45) Date of Patent: Feb. 18, 2025

(54) ***ARISTERIA* PLANT NAMED 'D CLASH'**

(50) Latin Name: *Aristeria beguinii*
Varietal Denomination: D CLASH

(71) Applicant: Deltacactus S.L., Amposta (ES)

(72) Inventor: Christian Jachertz, Amposta (ES)

(73) Assignee: Deltacactus S.L. (ES)

( * ) Notice: Subject to any disclaimer, the term of this patent is extended or adjusted under 35 U.S.C. 154(b) by 0 days.

(21) Appl. No.: 18/668,283

(22) Filed: May 20, 2024

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
CPC ..... A01H 6/00; A01H 5/12
See application file for complete search history.

*Primary Examiner* — Keith O. Robinson
(74) *Attorney, Agent, or Firm* — Cassandra Bright

(57) ABSTRACT

A new and distinct *Aristeria* cultivar named 'D CLASH' is disclosed, characterized by a superb rosette shape with a unique leaf pattern of green with white lenticel dots and a fully white longitudinal leaf rim. The striking leaf color contrast combined with the attractive rosette shape make the new variety exceptionally ornamental.

3 Drawing Sheets

Latin name of the genus and species: *Aristeria beguinii.*
Variety denomination: 'D CLASH'.

BACKGROUND OF THE INVENTION

The new variety *Aristeria beguinii* 'D CLASH' was selected as a naturally occurring, whole plant mutation of the unnamed parent plant *Aristeria beguinii*, the species itself. The new variety was discovered by the inventor in May 2018, at a nursery in Terragona, Spain.

Asexual reproduction of the new cultivar 'D CLASH' was first performed at a nursery in Terragona, Spain by leaf cuttings of original plant in March 2019. Through subsequent asexual propagation, approximately 4 generations have been reproduced, which have shown that the unique features of this cultivar are stable and reproduced true to type.

SUMMARY OF THE INVENTION

The cultivar 'D CLASH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'D CLASH.' These characteristics in combination distinguish 'D CLASH' as a new and distinct *Aristeria* cultivar:

1. Unique leaf pattern of green with white lenticel dots and a fully white longitudinal leaf rim.
2. Superb rosette shape.
3. Striking color contrast in leaves between green background and white lenticels and longitudinal leaf rim.

PARENT COMPARISON

Plants of the new cultivar 'D CLASH' are similar to the parent variety, in many horticultural characteristics. However the new variety, 'D CLASH' differs from parent in the following characteristics:

1. Leaf color of the new variety is a lighter green than the leaf color of the parent.
2. Leaf variegation of the new variety is green with white lenticel dots and a fully white longitudinal leaf rim. Leaf variegation of the parent is green with white lenticel dots but without a white longitudinal leaf rim.

COMMERCIAL COMPARISONS

The new variety can be compared to the commercial variety *Gasteria* 'D Due', U.S. Plant Pat. No. 29,665 as the varieties are similar in many horticultural characteristics. Plants of 'D Clash', however, differ from plants of 'D Due' in the following characteristics:

1. Leaf margins of the new variety are dentate, while leaf margins of this comparator are smooth.
2. Leaf variegation of the new variety is green with white lenticel dots and a fully white longitudinal leaf rim. Leaf variegation of this comparator is green with white lenticel dots but without a white longitudinal leaf rim.

'D CLASH' can be compared with the commercial variety x *Gasteraloe* 'D Delta', U.S. Plant Pat. No. 30,905 as the varieties are similar in many horticultural characteristics. However the new variety, 'D CLASH' differs from 'D Delta' in the following characteristics:

1. Leaf variegation of the new variety is green with white lenticel dots and a fully white longitudinal leaf rim. Leaf variegation of this comparator is green with white lenticel dots but without a white longitudinal leaf rim.

BRIEF DESCRIPTION OF THE PHOTOGRAPHS

The accompanying photograph in FIG. 1 illustrates in full color a typical plant of 'D CLASH' grown in a commercial greenhouse in Amposta, Spain. The plant is in a 9-cm pot, at approximately 40-weeks old.

Figure 1:
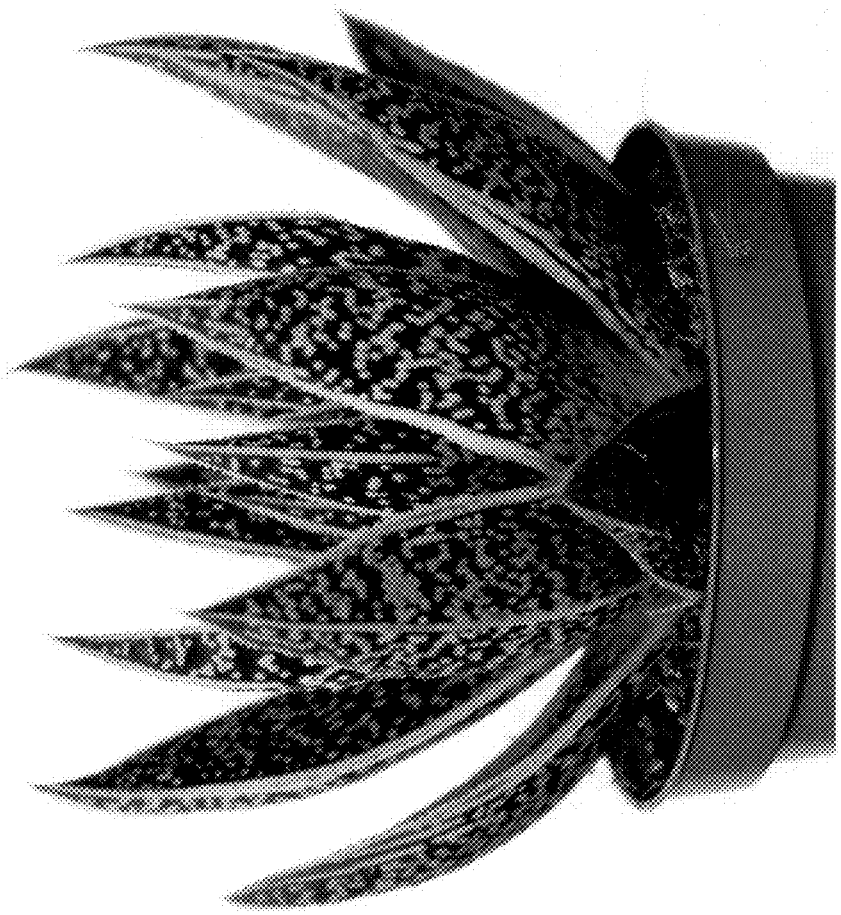
Figure 2:
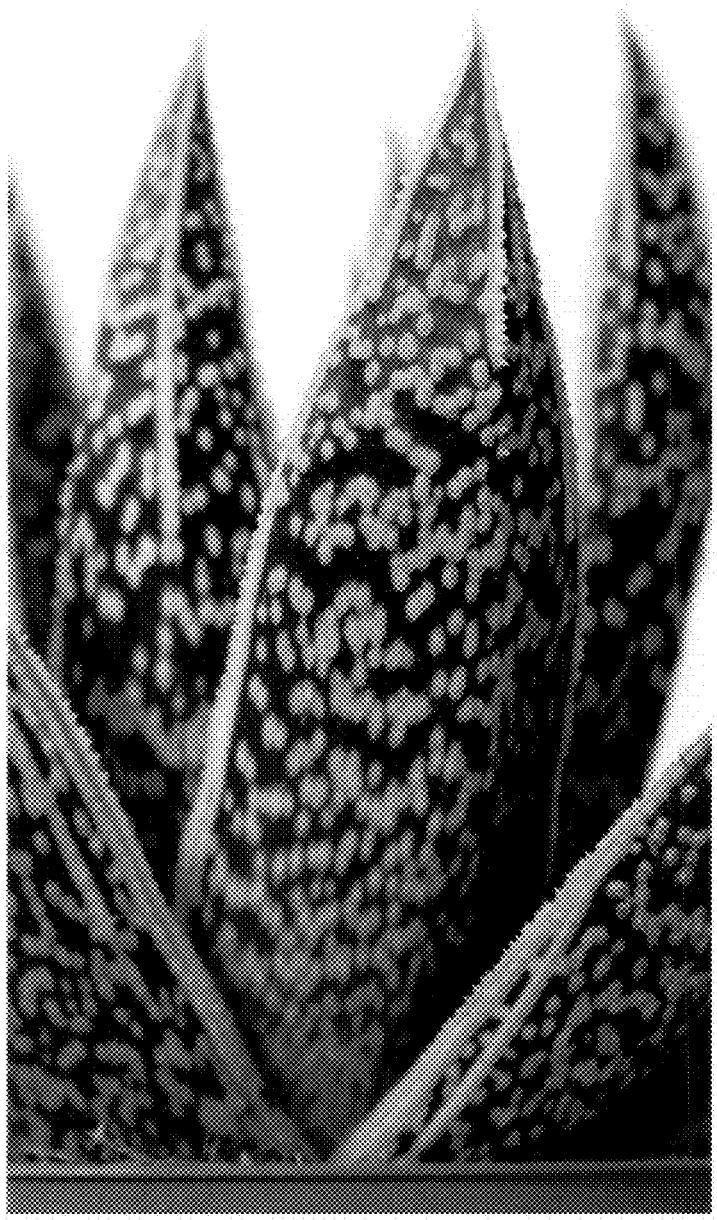
FIG. 2 illustrates a close-up of the underside of the leaf.
Figure 3:
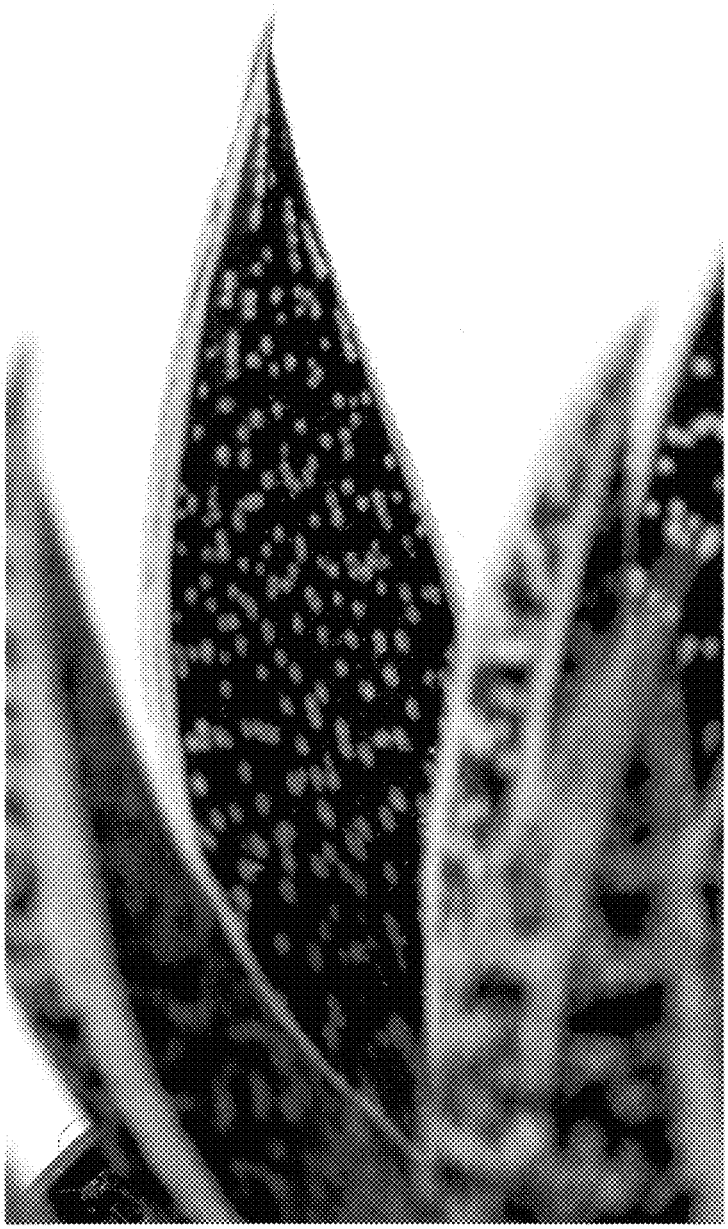
FIG. 3 illustrates a close-up of the upper side of the leaf.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'D CLASH' plant grown in a glass greenhouse in Amposta, Spain. The plant is approximately 40 weeks old in an 8.5 cm pot. Temperatures ranged between 18° C. to 20° C. during the day and 15° C. to 18° C. at night. No chemical treatments were given to the plants. Measurements and numerical values represent averages of typical plant types. Botanical classification: *Aristeria beguinii* 'D CLASH'.

PROPAGATION

Time to initiate roots: 20 days in summer at approximately 20° C.; 30 days in winter at 20° C.

Time to produce rooted cutting: 70 days in summer at approximately 20° C.; 85 days in winter at 20° C.

Time to finishing: Approximately 50 weeks from propagation to saleable plant.

Root description: Moderately dense, thick, fibrous, non-herbaceous, and moderately branching. Colored white, not accurately measured with R.H.S. chart.

PLANT

Plant type: Perennial potted plant.

Growth habit: Basal rosette.

Plant shape: Broad obovate to flattened globular (basal rosette).

Height: Approximately 9.1 cm.

Plant spread: Approximately 12 cm.

Growth rate: Low to moderate.

Branching habit: Basal rosette.

Primary branches: 1 basal rosette per plant; no lateral branches.

FOLIAGE

Leaf:

*Arrangement*.—Rosette.

*Quantity*.—Average 22 leaves per rosette.

*Average length*.—8.2 cm.

*Average width*.—2.5 cm.

*Shape*.—Broad lanceolate to near oblong, succulent.

*Aspect*.—Very slightly concave.

*Apex*.—Narrow apiculate to narrow acute, with a soft mucronate tip.

*Base*.—Broad cuneate.

*Margin*.—Finely densely serrate-dentate, average length of teeth: 0.75 mm; average height of teeth: 0.5 mm, colored RHS Greyed-Green 190C.

*Texture*.—Top surface: Moderately pustulate, placed randomly on lamina, average length: 1.5 mm, average diameter: 0.75 mm, average height: 0.3 mm colored RHS Greyed-Green 191C, fading lighter towards the base to 192A. Bottom surface: Densely pustulate, placed randomly on lamina, average length: 2.0 mm, average diameter: 0.75 mm, average height: 0.3 mm and less, colored RHS Greyed-Green 191C, fading lighter towards the base to 191D. In many leaves a line of elongated teeth is present on the midrib, near the leaf top and a secondary line of serrate-dentate teeth is present, parallel to the leaf margin, average length of teeth: 0.75 mm, average height of teeth: 0.5 mm, colored Greyed-Green 190C.

*Rugosity*.—Both sides non-rugose.

*Luster*.—Both sides slightly glossy.

*Pubescence*.—None.

*Color*.—Young foliage upper side: RHS Green NN137A, fading towards the base to Yellow-Green 145A. Young foliage under side: RHS Green NN137A, fading towards the base to Yellow-Green 144A and 144B. Mature foliage upper side: RHS Yellow-Green 147A to Greyed-Green N189A, fading to Greyed-Green 194B towards the base. Mature foliage under side: RHS Green NN137A to Yellow-Green 147A, fading to Greyed-Green 193A towards the base.

*Venation*.—Type: Parallel. Color: Mature, upper side: RHS Yellow-Green 147A to Greyed-Green N189A, fading to Greyed-Green 194B towards the base. Mature, under side: RHS Green NN137A to Yellow-Green 147A, fading to Greyed-Green 193A towards the base.

Other leaf characteristics: Leaves succulent, average thickness: 1.0 cm.

FLOWERS

None observed to date.

OTHER CHARACTERISTICS

Fruit/seed production: No fruits/seeds detected to date.

Disease and pest resistance: Neither resistance nor susceptibility to normal diseases and pests found in *Aristeria* varieties.

Tolerance to wind: High.

Tolerance to rain: Low.

Temperature tolerance: Observed to tolerate temperatures between 10° C. to 35° C.

What is claimed is:

1. A new and distinct cultivar of *Aristeria* plant named 'D CLASH' as herein illustrated and described.

* * * * *